(12) United States Patent
Bozeman et al.

(10) Patent No.: US 11,918,485 B2
(45) Date of Patent: *Mar. 5, 2024

(54) DEVICES AND TECHNIQUES FOR HIP REVISION SURGERY

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Michael Bozeman, Austin, TX (US); Monali Shah, Memphis, TN (US); Roy Messina, Memphis, TN (US); Andrea Karduss, Memphis, TN (US); Jeffrey J. Shea, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 18/079,516

(22) Filed: Dec. 12, 2022

(65) Prior Publication Data
US 2023/0114868 A1 Apr. 13, 2023

Related U.S. Application Data

(63) Continuation of application No. 17/080,193, filed on Oct. 26, 2020, now Pat. No. 11,576,791.
(Continued)

(51) Int. Cl.
*A61F 2/46* (2006.01)
*A61B 17/16* (2006.01)
*A61B 17/00* (2006.01)

(52) U.S. Cl.
CPC ........ *A61F 2/4609* (2013.01); *A61B 17/1666* (2013.01); *A61B 2017/00146* (2013.01);
(Continued)

(58) Field of Classification Search
CPC ........ A61F 2/46; A61F 2/4603; A61F 2/4609; A61F 2002/4619; A61F 2002/462;
(Continued)

(56) References Cited

U.S. PATENT DOCUMENTS

| | | | | |
|---|---|---|---|---|
| 5,318,570 A | * | 6/1994 | Hood | A61B 17/8847 601/2 |
| 5,382,251 A | * | 1/1995 | Hood | A61N 7/00 606/86 R |

(Continued)

FOREIGN PATENT DOCUMENTS

| | | | | |
|---|---|---|---|---|
| JP | 2010000336 A | * | 1/2010 | ............ A61B 17/16 |
| JP | 2010000336 A | | 1/2010 | |

(Continued)

OTHER PUBLICATIONS

Oscar, Operative Technique, Ultrasonic Arthroplasty Revision, Orthosonics Ltd, www.orthofix.com, Jan. 2016.
(Continued)

*Primary Examiner* — Eric S Gibson
(74) *Attorney, Agent, or Firm* — KDW Firm PLLC

(57) ABSTRACT

Piezoelectric osteotomy devices and corresponding systems and methods for removing an acetabular cup or shell from a patient's acetabulum are disclosed. In one embodiment, the piezoelectric osteotomy device includes a piezoelectric element to actuate a cutting tip on an armature. In some such embodiments, the cutting tip may be extended and/or retracted to facilitate cutting of bone around an acetabular cup. The armature may include a fluid output port located proximate the cutting tip to mitigate heat generated by the
(Continued)

cutting tip. In one embodiment, the piezoelectric osteotomy device is arranged and configured to provide constant current adjustment.

28 Claims, 8 Drawing Sheets

Related U.S. Application Data

(60) Provisional application No. 62/926,925, filed on Oct. 28, 2019.

(52) U.S. Cl.
CPC ............ *A61B 2017/00402* (2013.01); *A61B 2217/007* (2013.01)

(58) Field of Classification Search
CPC ....... A61B 17/14; A61B 17/142; A61B 17/32; A61B 17/320068; A61B 2017/320074; A61B 2017/320075; A61B 2017/320077; A61B 2017/320082
See application file for complete search history.

(56) References Cited

U.S. PATENT DOCUMENTS

| | | | |
|---|---|---|---|
| 8,419,640 B1 | 4/2013 | Saha | |
| 9,770,279 B2 * | 9/2017 | Kellar | A61F 2/4607 |
| 11,576,791 B1 * | 2/2023 | Bozeman | A61B 17/1666 |
| 2009/0024161 A1 * | 1/2009 | Bonutti | A61B 17/8872 |
| | | | 606/213 |
| 2013/0071813 A1 | 3/2013 | Braegger et al. | |
| 2017/0172610 A1 * | 6/2017 | Ishikawa | A61F 2/32 |
| 2018/0028248 A1 | 2/2018 | Hallab | |
| 2018/0146975 A1 * | 5/2018 | Zhang | A61B 17/320068 |
| 2023/0114868 A1 * | 4/2023 | Bozeman | A61B 17/1628 |
| | | | 606/81 |

FOREIGN PATENT DOCUMENTS

| | | |
|---|---|---|
| WO | 9222259 A2 | 12/1992 |
| WO | WO-9222259 A2 * | 12/1992 ......... A61B 17/8847 |

OTHER PUBLICATIONS

Salami, A., et al., "Piezosurgery in Otologic Surgery: Four years of experience," Journal of Otolaryngology—Head and Neck Surgery, 140(3): 412-418, Mar. 2009.

Crippa, B., et al., "Comparison of Postoperative Pain: Piezoelectric Device Versus Microdrill," Eur Arch Otorhinolaryngol, 268:1279-1282 (2011).

Grauvogel, J., et al., "Use of Piezosurgery for Removal of Retrovertebral Body Osteophytes in Anterior Cervical Discectomy," The Spine Journal, 14: 628-636 (2014).

Koc, B., "Comparison of Clinical Outcomes using a Piezosurgery Device vs. a Conventional Osteotome for Lateral Osteotomy in Rhinoplasty," ENT-Ear, Nose & Throat Journal, p. 318-326, Aug. 2017.

Pappalardo, S., et al., "Randomized Clinical Study Comparing Piezosurgery and Conventional Rotatory Surgery in Mandibular Cyst Enucleation," Journal of Cranio-Maxillo-Facial Surgery, 42:e80-e85 (2014).

Spinelli, G., et al., "Comparison of Piezosurgery and Traditional Saw in Bimaxillary Orthognathic Surgery," Journal of Cranio-Maxillo-Facial Surgery, 42:1211-1220 (2014).

Hoigne, D. et al., "Piezoelectric osteotomy in hand surgery: first experiences with a new technique," BMC Musculoskeletal Disorders, 7(36): 1-4, (2006).

* cited by examiner

100

MEDICAL DEVICE 102

BODY 104

ACTUATION MECHANISM 106

| SIGNAL CONDITIONER 108 | PIEZOELECTRIC ELEMENT 110 | MOTION AMPLIFIER 112 |

| DRIVE SIGNAL INPUT 114 | FLUID INPUT PORT 116 | USER INTERFACE 118 | EXTENSION MECHANISM 120 |

ARMATURE 122

| FLUID CHANNEL 124 | FLUID OUTPUT PORT 124 | CUTTING TIP 128 |

FIG. 1

DEVICES AND TECHNIQUES FOR HIP REVISION SURGERY

CROSS-REFERENCE TO RELATED APPLICATIONS

This application is a continuation of pending U.S. application Ser. No. 17/080,193, filed Oct. 26, 2020, which is a non-provisional of, and claims the benefit of the filing date of, U.S. provisional patent application No. 62/926,925, filed Oct. 28, 2019, entitled "Devices and Techniques for Hip Revision Surgery" the entirety of each application is incorporated by reference herein in its entirety.

FIELD OF THE DISCLOSURE

The present disclosure relates generally to devices and techniques for hip revision surgery, and particularly to piezoelectric osteotomy devices and techniques for acetabular shell removal during hip revision surgery.

BACKGROUND OF THE DISCLOSURE

Articulating regions of the anatomy can include areas where two bone sections move relative to one another. For example, an acetabulum, or pelvis, can provide a region for articulation with a femoral head. Sometimes, the articulating region, typically referred to as the hip joint, can become injured or worn, but it can be replaced with various prostheses. Such prostheses can replace the acetabulum, the femoral head, and various other portions of the femur, or other combinations thereof. The replacement of both the acetabulum and the femoral head is generally referred to as a total joint replacement.

Acetabular prostheses are one type of prosthesis currently used in joint replacement. Generally speaking, an acetabular prosthesis includes an acetabular cage coupled via, for example, an adhesive, to an acetabular cup implanted in the acetabulum. Sometimes, a revision surgery is performed to address issues with a previously implanted acetabular cup. Frequently, the acetabular cup must be removed during such revision surgeries. However, damage to bone and/or surrounding vasculature (e.g., iliac, obturator, pudendal, and/or gluteal vessels) often results from removing the acetabular cup.

It is with this in mind that the present disclosure is provided.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides a medical device including an armature comprising a cutting tip and a body coupled to the armature. The body may include an actuation mechanism with a piezoelectric element, a user interface, and an extension mechanism configured to extend the cutting tip and/or the armature based on operation of the user interface. In one embodiment, the armature and/or the cutting tip may be configured to match a curvature of an acetabular cup. In one embodiment, extension of the cutting tip is configured to follow a curvature of an acetabular cup. In one embodiment, the armature may comprise a curvilinear armature.

In one embodiment, the actuation mechanism with the piezoelectric element may be configured to move the cutting tip at a frequency and amplitude based on operation of the user interface. The frequency of the motion of the cutting tip may be between 22 to 29 kilohertz. In some embodiments, the frequency of the cutting tip may be between 15 and 40 kilohertz. The amplitude of the motion of the cutting tip may be between 60 and 210 micrometers. In one embodiment, one or more of the frequency and the amplitude are selectable.

In one embodiment, the piezoelectric element may include one or more ceramic discs. In one embodiment, the actuation mechanism may comprise a motion amplifier to translate motion of the piezoelectric element into motion of the cutting tip. In one embodiment, the motion of the cutting tip may have a larger amplitude than the motion of the piezoelectric element.

In one embodiment, the armature may comprise a fluid output port configured to deliver fluid proximate the cutting tip based on operation of the user interface. In one embodiment, the body may include a fluid input port configured to couple with a fluid source, wherein the fluid input port is in fluid communication with the fluid output port, at least in part, via a fluid channel in the armature.

In one embodiment, the body may comprise a drive signal input configured to couple with a signal generator. In one embodiment, the actuation mechanism is configured to apply an electromagnetic field to the piezoelectric element based on a signal received via the drive signal input to cause motion in the cutting tip. In one embodiment, the extension mechanism may include a worm gear.

The present disclosure provides a method comprising operating, via a user interface, an actuation mechanism with a piezoelectric element comprised in a body to cause motion in a cutting tip included in an armature coupled to the body. In one embodiment, the method may include extending the armature and/or cutting tip. In one embodiment, the method may include causing fluid to exit a fluid output port proximate the cutting tip based on operation of the user interface. In one embodiment, the method may include operating the user interface to extend the cutting tip and/or the armature. In one embodiment, extension of the cutting tip may be configured to follow the curvature of the acetabular cup. In one embodiment, the method may include controlling one or more of amplitude and frequency of motion in the cutting tip based on operation of the user interface.

Embodiments of the present disclosure provide numerous advantages. For example, in accordance with the present disclosure, devices, systems, and methods for reducing bone and/or vasculature damage during removal of an acetabular implant is provided.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 1 includes a block diagram of an exemplary medical device, according to one or more embodiments described herein;

Figure 2A:
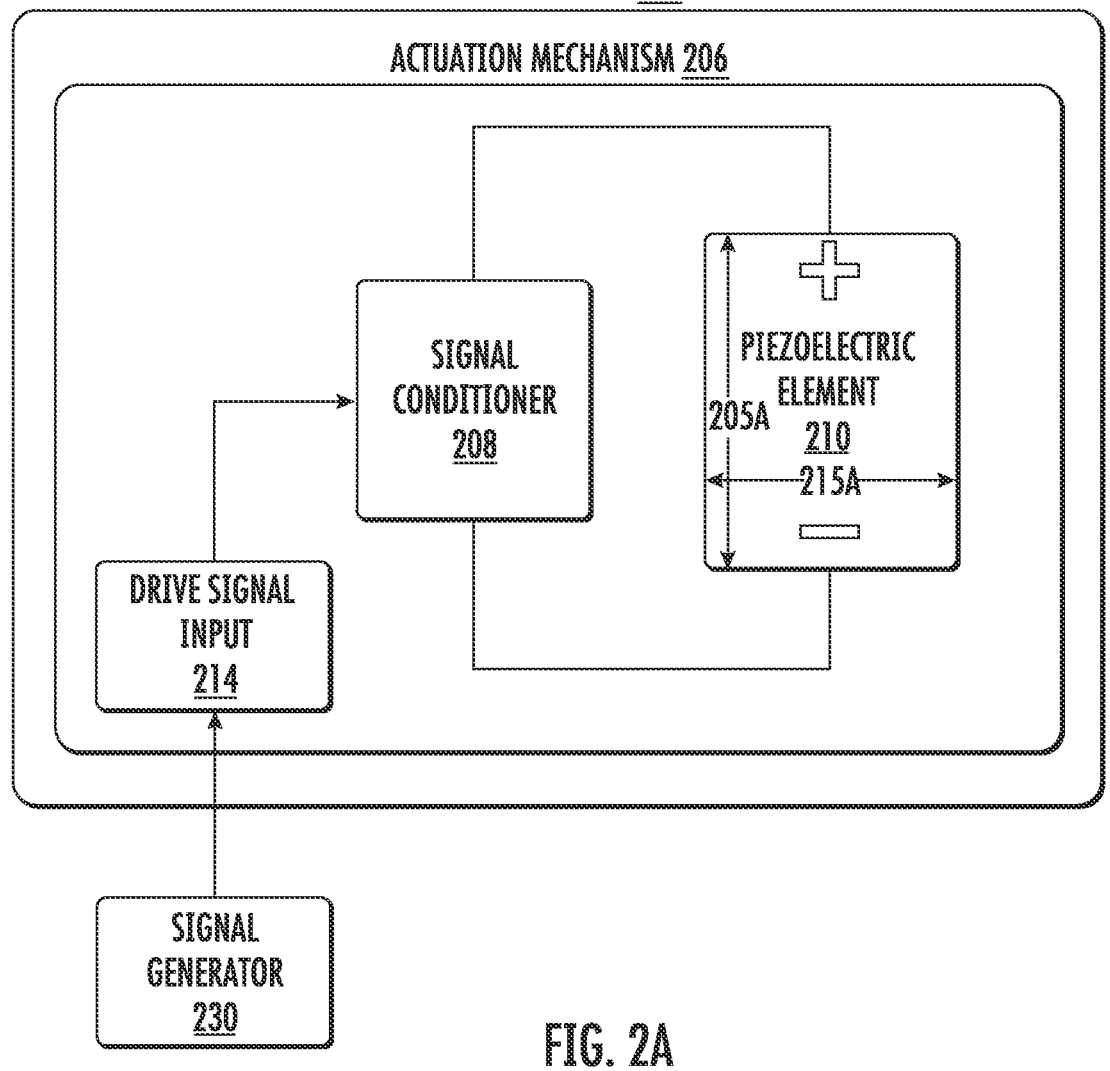
FIGS. 2A-2C illustrate various features of an exemplary actuation mechanism for a medical device, according to one or more embodiments described herein.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

Various features or the like of a piezoelectric osteotomy device arranged and configured to remove an acetabular cup or shell from a patient's acetabulum will now be described more fully hereinafter with reference to the accompanying drawings, in which one or more features of the piezoelectric osteotomy device will be shown and described. It should be appreciated that the various features may be used independently of, or in combination, with each other. It will be appreciated that a piezoelectric osteotomy device and corresponding systems and methods as disclosed herein may be embodied in many different forms and should not be construed as being limited to the embodiments set forth herein. Rather, these embodiments are provided so that this disclosure will convey certain features of the piezoelectric osteotomy device and accompanying system and method to those skilled in the art.

Embodiments of improved devices and techniques for hip revision surgery will now be described more fully hereinafter with reference to the accompanying drawings. Various embodiments are generally directed to piezoelectric osteotomy devices, systems, and methods for removing an acetabular cup or shell (used interchangeably herein without the intent to limit) from a patient's acetabulum while minimizing disruption to the existing, potentially compromised host bone. In one embodiment, the piezoelectric osteotomy device includes a piezoelectric element arranged and configured to actuate a cutting tip on an armature. In some such embodiments, the armature and/or the cutting tip may be extended and/or retracted to facilitate cutting of bone around the acetabular cup. The armature may include a fluid output port located proximate the cutting tip to mitigate heat generated by the cutting tip. These and other embodiments are described and claimed.

Some challenges facing hip revision surgery include removing the acetabular cup without causing excess damage to the surrounding bone and/or vasculature. These challenges may result from the growth of bone around an implanted acetabular cup, which includes cancellous bone that is more fragile than cortical bone in the rest of the pelvis. Additionally, the acetabulum is heavy in vasculature, which can lead to increased blood loss and higher vessel damage. Adding further complexity, many techniques for acetabular cup removal incorporate torque/mechanically operated instruments, leading to undue bone damage and vasculature damage. For example, a surgeon may attach an instrument to the acetabular cup, and pull it out, resulting in excessive removal of bone attached to the acetabular cup. Further, torque/mechanically operated instruments are imprecise and require unnecessary physical exertion to operate. These known techniques present great risk to the pelvic area of a patient because of the fragile bone and heavily vasculature around the acetabular cup. These and other factors may result in devices, systems, and methods for hip revision surgery that are difficult to use, unsafe, inaccurate, inefficient, and unreliable, resulting in limited applicability and/or uncertain outcomes. Such limitations can drastically reduce the dependability, ergonomics, effectiveness, and safety of hip revision surgeries, contributing to reduced usability, adverse outcomes, excess fatigue, and lost revenues.

Various embodiments described herein include piezoelectric osteotomy devices, components, and techniques that enable high precision acetabular shell removal during hip revision surgery that limits damage to bone and/or vasculature. Further, limiting damage to vasculature can reduce bleeding and improve visibility. In many embodiments, a piezoelectric element may operate a cutting tip at a selectable frequency to limit damage. For example, the cutting tip may be operated at a frequency to cut bone, which may be unique from a frequency to cut vasculature and soft tissue. In many embodiments, the cutting tip may extend out of an armature such as, for example, to allow for curvilinear osteotomy that matches the curvature of the acetabular cup.

In several embodiments, devices may include plumbing to enable fluid to be delivered proximate the cutting tip, such as for cooling and/or irrigation. For instance, cooling fluid may be delivered proximate the cutting tip to prevent thermal necrosis. In many embodiments, flow of the fluid may be controlled with the same interface as the piezoelectric element, providing a 2-in-1 system that is intuitive, ergonomic, and convenient. In many such embodiments, the flow of fluid, frequency of the cutting tip, extension of the cutting tip, and/or extension of the armature may be controlled with one hand or finger. In various embodiments, one or more of the components may be designed to simplify manufacturability, configurability, and/or adaptability. For example, cutting tips may be replaceable/exchangeable such as to allow different cutting tips to be utilized at different frequencies. In some embodiments, one or more components may be designed to work with existing devices, such as a signal generator or fluid source in an operating room. In these and other ways, components/techniques described here may improve operator experience, decrease learning curves, increase reliability, limit bone/vasculature damage, improve outcomes, and/or decrease recovery time for hip revision surgeries via realization of more efficient and valuable devices, systems, and methods for hip revision surgery.

FIG. 1 illustrates a block diagram of an exemplary medical device 102 in environment 100, according to one or more embodiments described herein. In some embodiments, one or more components of environment 100 may be the same or similar to one or more other components described herein. Environment 100 may include medical device 102 with body 104 and armature 122. The body 104 may include one or more of an actuation mechanism 106, a drive signal input 114, a fluid input port 116, a user interface 118, and an extension mechanism 120. The actuation mechanism 106 may also include a signal conditioner 108, a piezoelectric element 110, and a motion amplifier 112. The armature 122 may include a fluid channel 124, a fluid output port 126, and a cutting tip 128. In several embodiments described herein, one or more components of the medical device 102 may interoperate to enable safe and efficient acetabular shell removal, such as during hip revision surgery. Embodiments are not limited in this context.

In various embodiments, the actuation mechanism 106 may be utilized to generate movement in the cutting tip 128 of the armature 122. For example, the signal conditioner 108 may apply an electric/magnetic field to the piezoelectric element 110 based on a drive signal received via the drive signal input 114 to generate movement in the cutting tip 128 of the armature 122. In various embodiments, the drive signal may be generated and provided to the drive signal input 114 by an electric signal generator. For example, an electric generator located in a medical facility, such as an operating room, may be used to generate the drive signal. In many embodiments, the drive signal may be an alternating current signal. In other embodiments, the drive signal may be a direct current signal. The signal conditioner 108 may generate an electromagnetic field to induce motion in the piezoelectric element 110 based on the drive signal. In some embodiments, the signal conditioner 108 may alter and/or control one or more characteristics of the drive signal. For instance, the signal conditioner 108 may amplify one or more features of the drive signal. In another, or additional, instance, the signal conditioner 108 may convert the drive signal from direct current to alternating current. In several embodiments, the actuation mechanism 106 may be enclosed by the body 104. In various embodiments, the actuation mechanism 106, or one or more components thereof, may be directly mounted to the body 104.

In many embodiments, signal conditioner 108 may induce forces and/or movement in the piezoelectric element 110 via exposure to an electromagnetic field generated from, or included in, the drive signal. In many such embodiments, the forces and/or movement in the piezoelectric element 110 may include one or more of linear, compression, strain, stress. In various embodiments, the piezoelectric element 110 may include a piezoelectric crystal that vibrates upon application of an electromagnetic field. In some embodiments, the piezoelectric element 110 may include one or more piezoelectric ceramic discs.

In one or more embodiments, the motion amplifier 112 may couple the piezoelectric element 110 to the armature 122. In many embodiments, the motion amplifier 112 may translate force and/or motion induced in the piezoelectric element 110 into motion of the cutting tip 128. For example, motion amplifier 112 may cause the motion of the cutting tip 128 to have a larger amplitude than the motion of the piezoelectric element 110. In some embodiments, the armature 122 may operate as, or include, a waveguide to facilitate the transfer of motion to the cutting tip 128. In various embodiments, one or more portions of the cutting tip 128 may operate as, or include, a waveguide to facilitate the transfer of motion to the distal end of the cutting tip 128. In some embodiments, the expected ultrasonic movements may be small and generally lateral. These movements may be amplified by a horn section comprised in the motion amplifier 112. In some embodiments, the ultrasonic movements may be amplified by the waveguide (e.g., armature 122 and/or cutting tip 128). For example, the waveguide may taper to the distal end of the cutting tip.

In several embodiments, motion of the cutting tip 128 may include one or more of a linear, reciprocating, angular, and/or hammering motions. In many embodiments, the actuation mechanism 106 may cause the cutting tip 128 to move at a specific frequency and/or amplitude or range of frequencies/amplitudes. For instance, the cutting tip 128 may be moved at a frequency and amplitude that will cut bone and not vasculature or soft tissue (e.g., frequency range of 22 to 29 kilohertz and amplitude range of 60 to 210 micrometers). In some embodiments, the frequency and/or amplitude of the cutting tip 128 may be controllable/selectable, such as via user interface 118. For instance, the frequency may be adjusted to above 50 kilohertz for cutting neurovascular tissue and/or other soft tissues.

As previously mentioned, the armature 122 may include a fluid channel 124 and a fluid output port 126. In many embodiments, the fluid output port 126 may be located proximate the cutting tip 128 and the fluid channel 124 may place the fluid output port 126 in fluid communication with the body 104 of the medical device 102. In various embodiments, the fluid input port 116 may enable a fluid from a fluid source to be supplied, or delivered, to the fluid output port 126 of the armature 122 via the fluid channel 124. In several embodiments, the fluid source may include a fluid pouch with a tube that connects to the fluid input port 116. In many embodiments, the body 104 may include plumbing to place the fluid input port 116 in fluid communication with the fluid channel 124 of the armature 122.

In various embodiments, the armature 122 and/or cutting tip 128 may be replaceable/selectable. In various such embodiments, a variety of armatures and/or cutting tips may be available to customize the configuration of the medical device 102 for specific needs. For example, an armature and/or cutting tip may be selected to match the degree of curvature for a specific acetabular cup. In another example, the cutting tip 128 may be selected based on the frequency and/or amplitude implemented by the actuation mechanism 106. In yet another example, the cutting tip 128 may be selected based on the type, or lack thereof, of fluid provided via the fluid output port 126. In some embodiments, the armature and/or cutting tip may be curvilinear. In one or more embodiments, the medical device (e.g., piezoelectric osteotomy device) 102 may be provided in a kit including a plurality of differently sized and/or configured armatures and/or cutting tips.

In some embodiments, the user interface 118 may be used to control fluid flow from the fluid input port 116 to the fluid output port 126. For example, the user interface 118 may be used to operate a pump, a valve, etc. to control fluid flow from the fluid input port 116 to the fluid output port 126. In one or more embodiments, fluid flow out of the fluid output port 126 may be utilized to remove, or at least minimize, heat from the cutting tip 128 or surrounding anatomy. For instance, the fluid may include refrigerated saline. In many embodiments, fluid flow out of the fluid output port 126 may be used to prevent thermal necrosis. In various embodiments, the temperature of the fluid may be selectable. For example, the fluid may be used to cyclically cool and heat an implant (e.g., acetabular cup) and/or the surrounding anatomy. In such examples, cyclically cooling and heating the implant and/or surrounding anatomy may assist in removal of the implant. In some embodiments, fluid flow and motion of the cutting tip 128 may be controlled by a common control in the user interface 118. For instance, a single actuating mechanism such as, for example, a button, may cause fluid to flow and actuation of the cutting tip 128.

In many embodiments, the extension mechanism 120 may enable extension and retraction of the armature 122 and/or the cutting tip 128. In some embodiments, the extension mechanism 120 may enable curvilinear osteotomy with the cutting tip 128 of the armature 122 that matches the curvature of an acetabular cup. In one or more embodiments, extension/retraction of the cutting tip 128 may be controlled via the user interface 118. In some embodiments, the extension mechanism 120 may utilize a worm gear to advance/retract the armature 122 and/or cutting tip 128, although other mechanisms for advancing and retracting the armature and/or cutting tip are envisioned. For example, a wheel may be rolled in a first direction to extend the cutting tip 128 and a second direction to retract the cutting tip 128 (see e.g., FIG. 3). In many embodiments, extension of the cutting tip 128 may enable a manual method to advance a curved blade along the back side of an ingrown acetabular shell.

In one or more embodiments, a shape memory material, such as a shape-memory metal, may be used to instantiate curvature in the armature 122 and/or cutting tip 128. In some embodiments, portions of the cutting tip 128 retracted into the armature 122 may be held in a straightened state by the armature, while portions of the cutting tip 128 extended out of the armature 122 may curve to match the curvature of an acetabular cup. In other words, the armature 128 may limit the amount of bend in portions of the cutting tip 128 until those portions are extended out of the armature. In various embodiments, the armature 122 and/or cutting tip 128 may be constructed from surgical grade stainless steel, titanium, and/or alloys thereof, although it is envisioned that the armature and/or cutting tip may be manufactured from any suitable material now known or hereafter developed. In some embodiments, the armature 122 and/or cutting tip 128 may be coated. For example, the cutting tip 128 may include a titanium nitride coated steel blade tip.

In several embodiments, the user interface 118 may include one or more actuating mechanisms such as, for examples, buttons, switches, controls, wheel, knobs, interface members, etc. or a combination thereof. For example, the user interface 118 may include one or more of a wheel to control extension/retraction of the cutting tip 128, a first knob to control the frequency of the cutting tip 128, a second knob to control the amplitude of the cutting tip 128, and a button to control start and stop movement of the cutting tip 128 as well as fluid flow out of the fluid output port 126. In some embodiments, the user interface 118 may provide feedback, such as the current frequency and/or amplitude setting of the cutting tip 128. In several embodiments, the body 104 may include a handle that allows for ergonomic hand placement for a user. Further, the handle, in conjunction with the user interface 118, may be configured to enable single-handed, or single-fingered, operation of the medical device 102. For example, single-handed blade extension may simplify maneuvering the cutting tip 128 around a span of an acetabular cup.

Figure 2B:
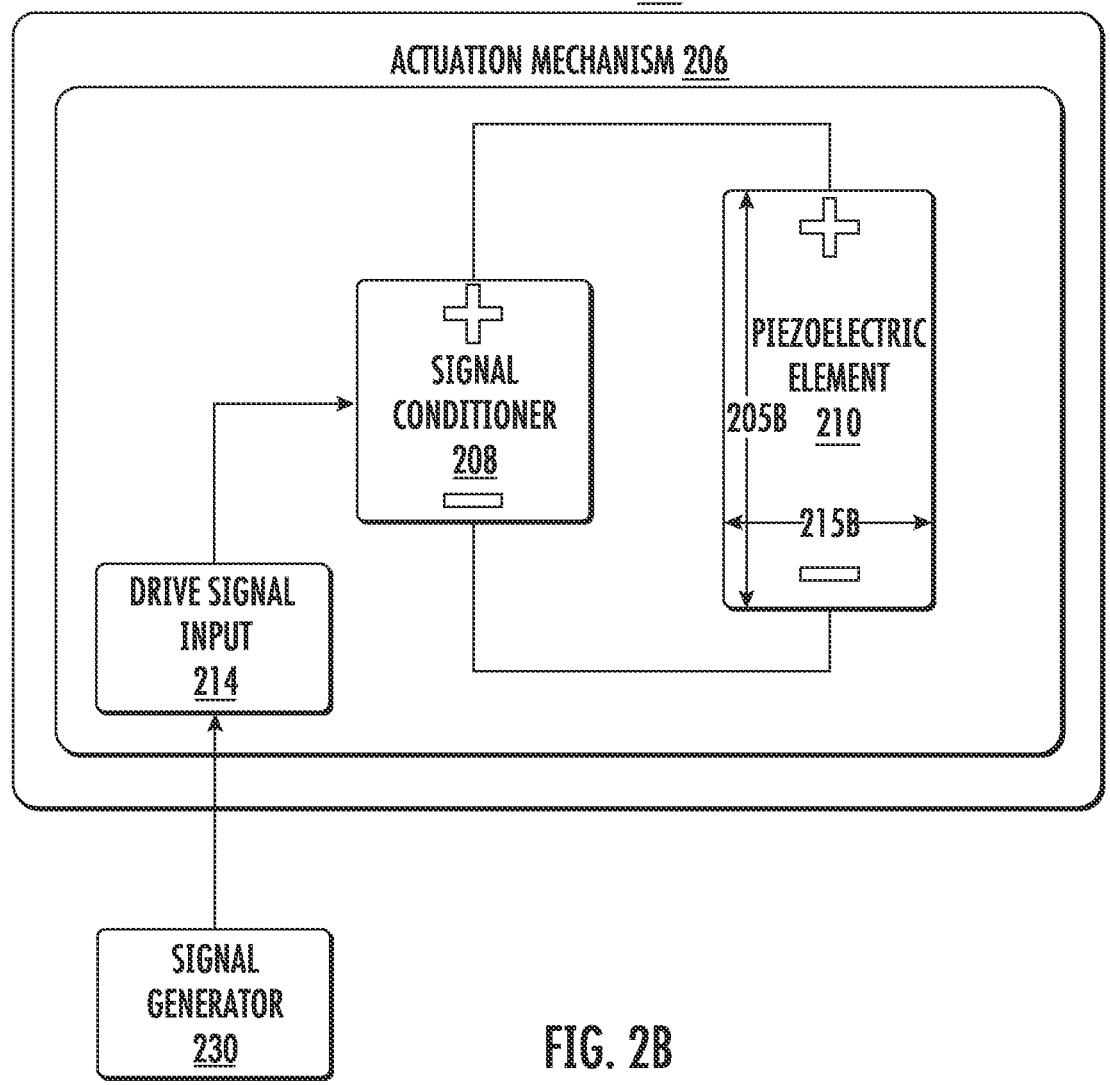
Figure 2C:
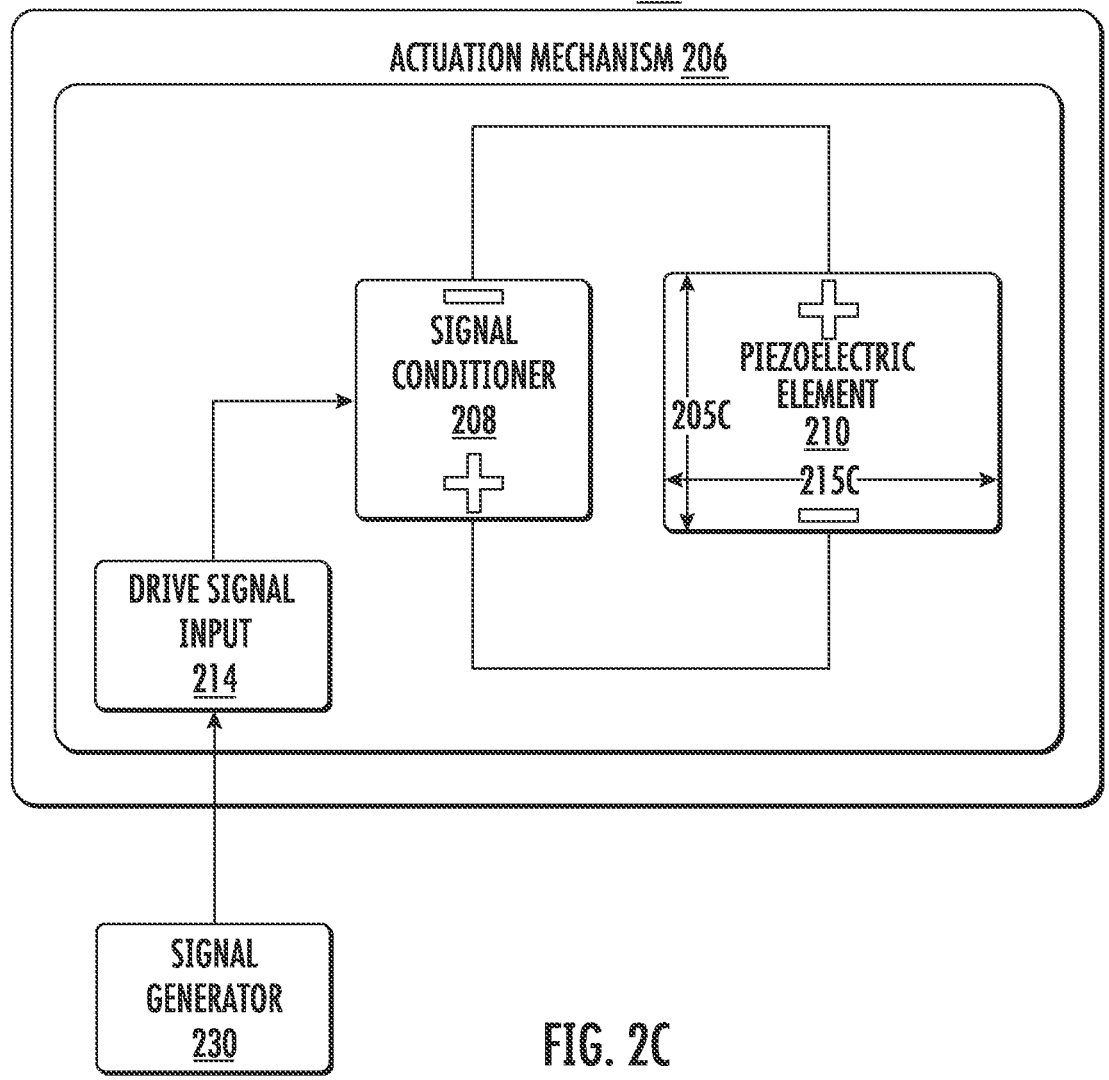

FIGS. 2A-2C illustrate an example of an embodiment of an actuation mechanism 206 for a medical device 202 in environments 200A, 200B, 200C, according to one or more embodiments described herein. In some embodiments, one or more components of environments 200A, 200B, 200C may be the same or similar to one or more other components described herein. Environments 200A, 200B, 200C may include signal generator 230 in conjunction with medical device 202. The medical device 202 may include actuation mechanism 206 with drive signal input 214, signal conditioner 208, and piezoelectric element 210. In many embodiments, the piezoelectric element 210 may be polarized with a positive pole located toward the top and a negative pole located toward the bottom. In one or more embodiments described herein, signal conditioner 208 may apply signals of different polarizations to cause deformation in piezoelectric element 210, such as via the reverse piezoelectric effect. In one or more such embodiments, these deformations may be used to cause a cutting motion in the cutting tip. Embodiments are not limited in this context.

Accordingly, in environment 200A, piezoelectric element 210 may have a first height 205A and a first width 215A. Further, actuation mechanism 206 may be in a standby state with no signal being applied to piezoelectric element 210. In environment 200B, piezoelectric element 210 may have a second height 205B and a second width 215B. Further, actuation mechanism 206 may be in a state with a positive-polarized signal being applied to piezoelectric element 210 via signal conditioner 208. In environment 200C, piezoelectric element 210 may have a third height 205C and a third width 215C. Further, actuation mechanism 206 may be in a state with a negative-polarized signal being applied to piezoelectric element 210 via signal conditioner 208. Accordingly, the height 205A may be less than the height 205B and greater than the height 205C; and the width 215A may be greater than the width 215B and less than the width 215C.

In one or more embodiments, the signal conditioner 208 or the signal generator 230 may comprise, or function as, a controlled voltage/current source. In various embodiments, the controlled voltage/current source may monitor current and/or voltage flowing to the piezoelectric element 210. In various such embodiments, the controlled voltage/current source may adjust the current and/or voltage flowing to the piezoelectric element 210 based on monitoring of the current and/or voltage flowing to the piezoelectric element 210. In several embodiments, the controlled voltage/current source may adjust the current/voltage flow to maintain a constant resonance in the cutting tip. In some embodiments, when resonating, the current and voltage waveforms may be out of phase (e.g., orthogonal) to each other. However, when not resonating, the current and voltage waveforms may be in phase with each other. Accordingly, in various embodiments, the controlled voltage/current source may maintain the current and voltage waveforms orthogonal with respect to each other.

In many embodiments, the controlled voltage/current source may adjust the current/voltage flowing to the piezoelectric element 210 to keep the cutting tip resonating in a safe and effective manner. For example, a drop in current may indicate the cutting tip is being dampened, such as when it is cutting bone. In such examples, the voltage may be increased to keep the cutting tip resonating. In another example, an increase is current may indicate the cutting tip is over resonating, such as when it is actuating without resistance (e.g., in the air). In such other examples, the current may be decreased to prevent damage to the actuation mechanism, the armature, and/or the cutting tip, such as due to over resonating.

In several embodiments, the piezoelectric element may include one or more of crystals, ceramics, berlinite, cane sugar, quartz, rochelle salt, topaz, tourmaline, bone, barium titanate, lead zirconate titanate, bismuth, gallium phosphate, and the like. In many embodiments, materials of the piezoelectric element 110 may be chosen to improve heat tolerance of the medical device 102. In some embodiments, high voltages may induce changes in the width of the piezoelectric element 210. In various embodiments, when the piezoelectric element 210 is subjected to an electrical and/or magnetic field, it may expand/contract in a direct proportion to the electrical and/or magnetic field. In many embodiments, application of electric/magnetic fields to the piezoelectric element 210 may facilitate a linear micro-motion of the cutting tip as opposed to a rotary macro-motion.

In various embodiments, one or more components of the medical device 102 may be constructed from materials selected based on their ability to handle ultrasonic stresses. In many embodiments, one or more portions of the waveguide, armature, and/or cutting tip may be constructed from metal, such as stainless steel or a titanium alloy, although other suitable materials now known or hereafter developed may be used. Typically, ultrasonic stresses may peak approximately an eighth or a sixteenth of a wavelength from the tip. Accordingly, some embodiments may include reinforcing approximately an eighth or a sixteenth of a wavelength from the tip.

For example, in various embodiments, steel and/or titanium may be selected. In connection with embodiments where titanium is used, with a resonant frequency of 23 kHz, in titanium (in which the speed of sound is 6070 m/s) an eighth of a wavelength from the tip would be, in one embodiment, approximately 3.42 cm and a sixteenth of a wavelength from the tip would be approximately 1.71 cm. In connection with embodiments where steel is used, with a resonant frequency of 23 kHz, in steel (in which the speed of sound is 5790 m/s) an eighth of a wavelength from the tip would be, in one embodiment, approximately 3.15 cm and a sixteenth of a wavelength from the tip would be approximately 1.57 cm.

In some embodiments, titanium may be used to save weight. For instance, titanium can be 45% lighter than steel. Further, titanium may be more durable and resistant to plastic deformation. Steel may be stronger, but fatigue easier than titanium. Titanium may be used to provide more heat tolerance than steel. Titanium may provide improved corrosion resistance. Further, titanium is nonmagnetic while steel is magnetic. In some embodiments, the nonmagnetic properties of titanium may be used to prevent interference with, or by, the piezoelectric element 110. In some embodiments, the magnetic properties of steel may be used to promote or utilize magnetic fields. Oftentimes, steel may be used where strength is needed in hard material and titanium may be used where a lightweight and strong material is needed. In one or more embodiments, steel may be used to reduce cost and enable disposable components. In some embodiments, the waveguide (e.g., armature and/or cutting tip) may be replaceable/disposable.

Figure 3:
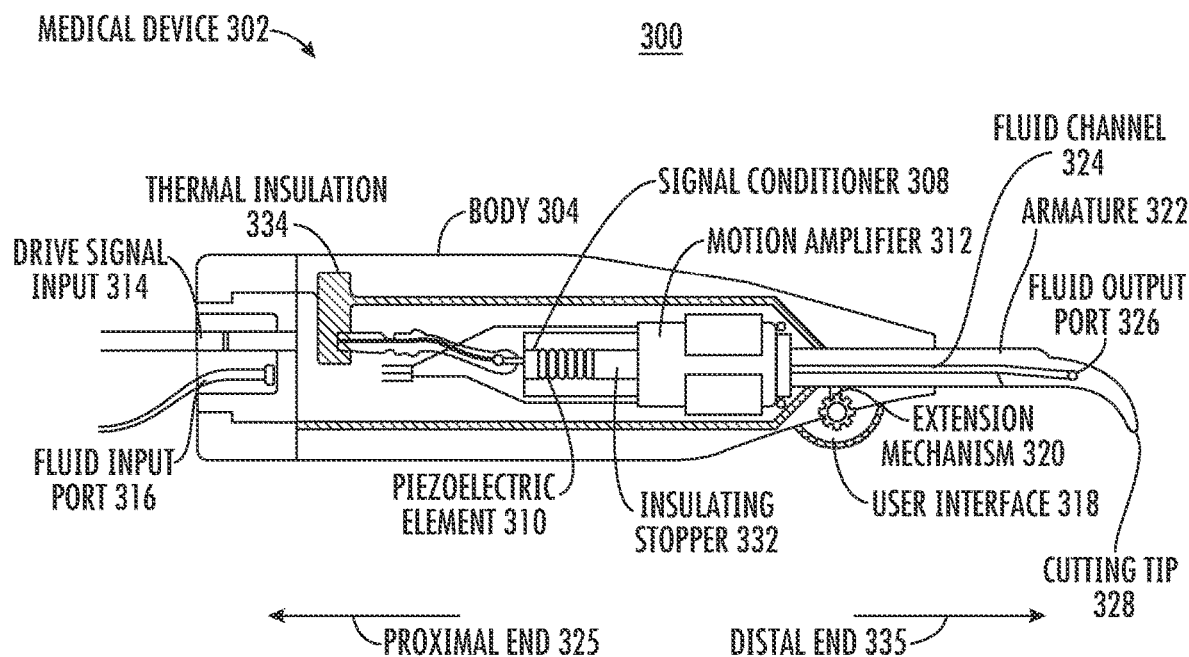
FIG. 3 illustrates an exemplary medical device, according to one or more embodiments described herein.

FIG. 3 illustrates an exemplary medical device 302 (e.g., a piezoelectric osteotomy device) in environment 300, according to one or more embodiments described herein. In some embodiments, one or more components of environment 300 may be the same or similar to one or more other components described herein. For example, medical device 102 may be the same or similar to medical device 302. Environment 300 includes medical device 302 with a proximal end 325 and a distal end 335. As shown, the medical device 302 may include a body 304 and an armature 322. The body 304 may include one or more of a drive signal input 314, a fluid input port 316, a user interface 318, an extension mechanism 320, thermal insulation 334, insulating stopper 332, and an actuation mechanism with a signal conditioner 308, a piezoelectric element 310, and a motion amplifier 312. The insulating stopper 332 may electrically isolate the actuation mechanism from armature 322 and/or cutting tip 328. For example, the insulating stopper 332 may insulate the cutting tip 328 from the electrical signal that drives the piezoelectric elements (e.g., the drive signal or signal based thereon) from conducting to the cutting tip 328 thus preventing the electrical signal from making direct contact with the patient via the cutting tip 328. The armature 322 may include a fluid channel 324, a fluid output port 326, and a cutting tip 328. In several embodiments described herein, one or more components of the medical device 302 may interoperate to enable safe and efficient acetabular shell removal, such as during hip revision surgery. For instance, the cutting tip 328 may extend out of the armature 322 with a curvature that matches the curvature of an acetabular cup (see e.g., FIG. 4). Embodiments are not limited in this context.

In the illustrated embodiment, user interface 318 may include a mechanism such as, for example, a wheel that can be rotated in a first direction to extend the cutting tip 328 and can be rotated in a second direction to retract the cutting tip 328. In many embodiments, the mechanism of the user interface 318 may operate the extension mechanism 320 to cause the cutting tip 328 to extend/retract. In some embodiments, the wheel may be depressed to cause motion in the cutting tip 328 and or fluid flow through the fluid output port 326. In various embodiments, the thermal insulation 334 may prevent, or limit, heat generated in the body 304 from heating the surface of the body 304 and/or the user interface 318. For example, the piezoelectric element 110 may generate heat that the user interface 118 is insulated from by thermal insulation 334. In some embodiments, the thermal insulation 334 may prevent, or limit, heat generated by the medical device 302 from heating cooling fluid provided from fluid input port 316 and delivered to fluid output port 326 via fluid channel 324.

In one or more embodiments, the medical device 102 may include a heat sink or heat exchanger to remove heat from the actuation mechanism 106. For instance, fluid may be circulated to remove heat from the piezoelectric element 110. Exposing the piezoelectric element 110 to excessive heat may cause depolarization, reduced effectiveness, and/or reduced component life. In many embodiments, materials in the piezoelectric element 110 may be chosen to improve heat tolerance.

Figure 4:
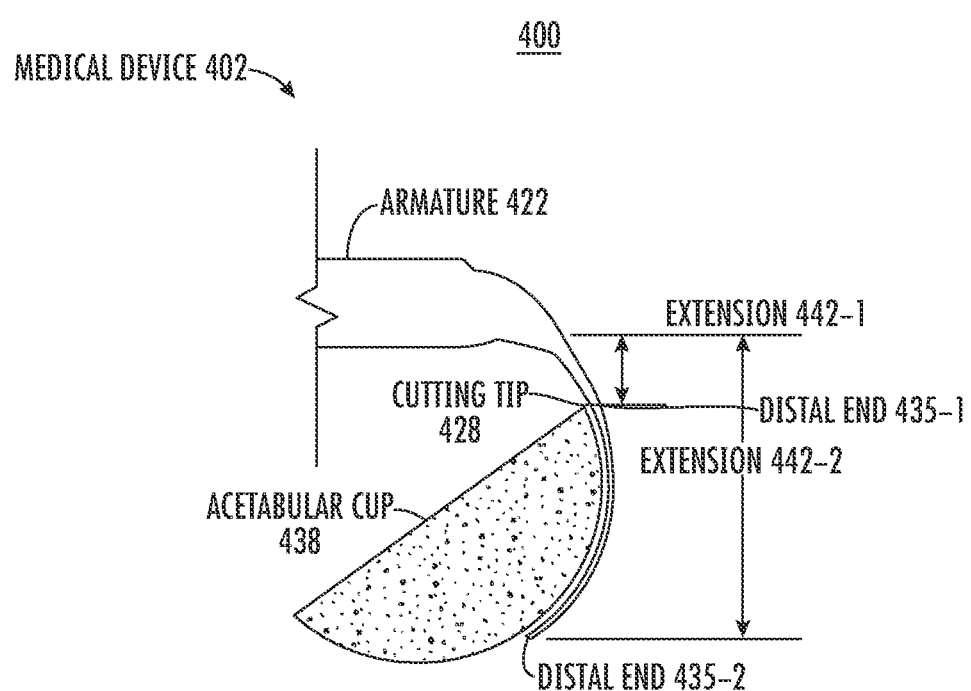
FIG. 4 illustrates various features of an exemplary medical device in conjunction with an acetabular cup, according to one or more embodiments described herein.

FIG. 4 illustrates various features of an exemplary medical device 402 in conjunction with an acetabular cup 438 in environment 400, according to one or more embodiments described herein. In some embodiments, one or more components of environment 400 may be the same or similar to one or more other components described herein. For example, medical device 402 may be the same or similar to medical device 302. Environment 400 illustrates a distal portion of medical device 402 with extensions 442-1, 442-2 of cutting tip 428 out of armature 422. Extension 442-1 may demonstrate positioning of the cutting tip 428 in a retracted state such that distal end 435-1 is the distal end of cutting tip 428. Extension 422-2 may demonstrate positioning of the cutting tip 428 in an extended state such that distal end 435-2 is the distal end of cutting tip 428. In one or more embodiments described herein, curvature of the extended portion of cutting tip 428 may match the curvature of the acetabular cup 438. Embodiments are not limited in this context.

In many embodiments, the medical device 402 may be operated to continuously transition the cutting tip 428 between extension 422-1 and extension 422-2. In many embodiments, extension 422-2 may position the distal end 435-2 at or beyond the apex of the acetabular cup 438. In many such embodiments, positioning the distal end 435-2 at or beyond the apex of the acetabular cup 438 enables access to all bone around the acetabular cup 438 with the cutting tip 428 by rotating the medical device 402 about the acetabular cup 438. In some embodiments, cutting tip 428 may be retracted further than extension 442-1 and/or extended further than extension 442-2. For example, the end of cutting tip 428 may be retracted all the way into armature 422. In such examples, retracting cutting tip 428 into armature 422 may prevent or limit unintended contact with or damage to the cutting tip 428. In many embodiments, a user interface of the medical device 402 may be operated to transition the cutting tip 428 from the retracted state to the extended state in a continuous manner to advance the cutting tip 428 along the back side of an ingrown acetabular shell.

Figure 5A:
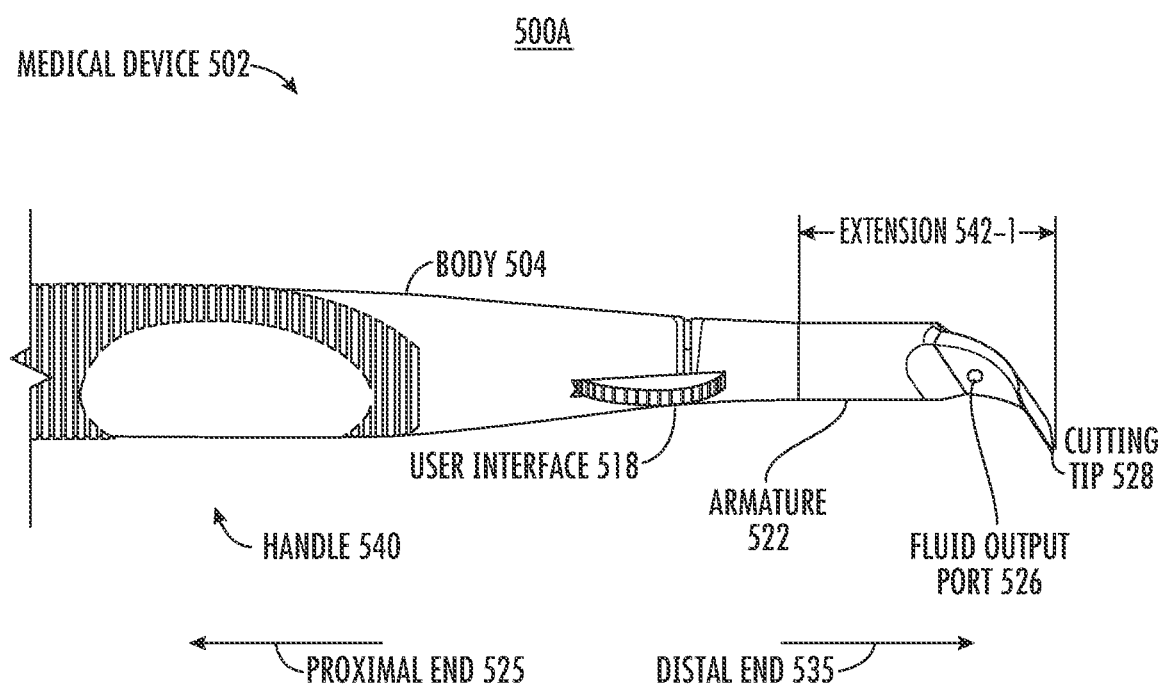
FIGS. 5A and 5B illustrate various features of an exemplary medical device, according to one or more embodiments described herein.
Figure 5B:
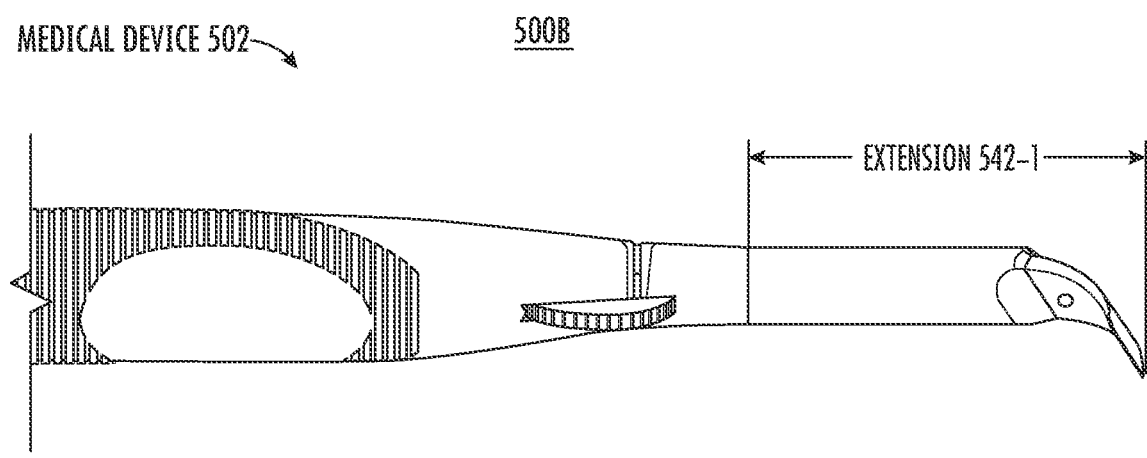

FIGS. 5A and 5B illustrate various features of an exemplary medical device 502 in environments 500A, 500B, according to one or more embodiments described herein. In some embodiments, one or more components of environments 500A, 500B may be the same or similar to one or more other components described herein. For example, medical device 502 may be the same or similar to medical device 402. Environments 500A, 500B include medical device 502 with a proximal end 525 and a distal end 535. The medical device 502 may include a body 504 with handle 540, a user interface 518, and an armature 522 with a fluid output port 526 and a cutting tip 528. In various embodiments, medical device 502 may enable linear extension of the armature 522. Embodiments are not limited in this context.

In one or more embodiments, medical device 502 may employ an alternative, or additional, type of extension than employed by medical device 402. In many embodiments, the type of extension employed by medical device 502 may be used to adjust for the anatomy of a patient. For instance, extension 542-2 may be utilized on patients with larger anatomies. In environment 500A, the armature 522 is illustrated in a retracted state with extension 522-1. In environment 500B, the armature 522 is illustrated in an extended state with extension 542-2. Accordingly, extension 542-1 may be less than extension 542-2. In one or more embodiments described herein, user interface 518 may be operated to transition the armature 522 from the retracted state to the extended state in a continuous manner.

In one or more such embodiments, user interface 518 may be operated with a single hand to transition the armature from the retracted state to the extended state. In some embodiments, the handle 540 may include one or more ergonomic features (e.g., grip, padding, textures, antimicrobial surfaces, finger grooves, and the like) to improve user experience. For instance, handle 540 may include features for enabling single-handed use or simplifying cleaning. In some instances, handle 540 may include features for enabling single-finger actuation of user interface 518. In one or more embodiments, medical device 402 may include one or more components/features that are the same or similar to those of medical device 502, such as body 504, user interface 518, fluid output port 526, and handle 540.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

Directional terms such as top, bottom, superior, inferior, medial, lateral, anterior, posterior, proximal, distal, upper, lower, upward, downward, left, right, longitudinal, front, back, above, below, vertical, horizontal, radial, axial, clockwise, and counterclockwise) and the like may have been used herein. Such directional references are only used for identification purposes to aid the reader's understanding of the present disclosure. For example, the term "distal" may refer to the end farthest away from the medical professional/operator when introducing a device into a patient, while the term "proximal" may refer to the end closest to the medical professional when introducing a device into a patient. Such directional references do not necessarily create limitations, particularly as to the position, orientation, or use of this disclosure. As such, directional references should not be limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof. Unless otherwise defined, all technical terms used herein have the same meaning as commonly understood by one of ordinary skill in the art to which the disclosure belongs.

The foregoing description has broad application. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. Furthermore, references to "one embodiment" of the present disclosure are not intended to be interpreted as excluding the existence of additional embodiments that also incorporate the recited features.

In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The phrases "at least one", "one or more", and "and/or", as used herein, are open-ended expressions that are both conjunctive and disjunctive in operation. The terms "a" (or "an"), "one or more" and "at least one" can be used interchangeably herein.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

The invention claimed is:

1. A cutting instrument, comprising
a body including:
   a cutting tip;
   an actuation mechanism operatively associated with a piezoelectric element;
   a user interface; and
   an extension mechanism configured to extend the cutting tip relative to the body based on operation of the user interface.

2. The cutting instrument of claim 1, wherein the cutting tip is configured to match a curvature of an acetabular cup.

3. The cutting instrument of claim 1, wherein extension of the cutting tip is configured to follow a curvature of an acetabular cup.

4. The cutting instrument of claim 1, wherein the actuation mechanism and the piezoelectric element are configured to move the cutting tip at a frequency and amplitude based on operation of the user interface.

5. The cutting instrument of claim 4, wherein the frequency is between 22 to 29 kilohertz.

6. The cutting instrument of claim 4, wherein the amplitude is between 60 and 210 micrometers.

7. The cutting instrument of claim 4, wherein one or more of the frequency and the amplitude are selectable.

8. The cutting instrument of claim 1, wherein the piezoelectric element comprises one or more ceramic discs.

9. The cutting instrument of claim 1, wherein the actuation mechanism comprises a motion amplifier to translate motion of the piezoelectric element into motion of the cutting tip.

10. The cutting instrument of claim 9, wherein the motion of the cutting tip has a larger amplitude than the motion of the piezoelectric element.

11. The cutting instrument of claim 1, wherein the body further includes a fluid output port configured to deliver fluid proximate the cutting tip based on operation of the user interface.

12. The cutting instrument of claim 11, wherein the body further includes a fluid input port configured to couple with a fluid source, wherein the fluid input port is in fluid communication with the fluid output port, at least in part, via a fluid channel.

13. The cutting instrument of claim 1, wherein the body further includes a drive signal input, the drive signal input configured to couple with a signal generator.

14. The cutting instrument of claim 13, wherein the actuation mechanism is configured to apply an electromagnetic field to the piezoelectric element based on a signal received via the drive signal input to cause motion in the cutting tip.

15. The cutting instrument of claim 1, wherein the extension mechanism comprises a worm gear.

16. A cutting instrument arranged and configured to cut a previously implanted acetabular cup from a patient's bone, the cutting instrument comprising
a body including:
   a curvilinear cutting tip configured to match a curvature of the acetabular cup;
   an actuation mechanism operatively associated with a piezoelectric element;
   a user interface; and
   an extension mechanism configured to extend the cutting tip relative to the body at a frequency and an amplitude based on operation of the user interface, the frequency being between 22 to 29 kilohertz.

17. The cutting instrument of claim 16, wherein extension of the cutting tip is configured to follow the curvature of the acetabular cup.

18. The cutting instrument of claim 16, wherein the amplitude is between 60 and 210 micrometers.

19. The cutting instrument of claim 16, wherein one or more of the frequency and the amplitude are selectable.

20. The cutting instrument of claim 16, wherein the piezoelectric element comprises one or more ceramic discs.

21. The cutting instrument of claim 16, wherein the actuation mechanism comprises a motion amplifier to translate motion of the piezoelectric element into motion of the curvilinear cutting tip.

22. The cutting instrument of claim 21, wherein the motion of the cutting tip has a larger amplitude than the motion of the piezoelectric element.

23. The cutting instrument of claim 16, wherein the body further includes:
- a fluid input port arranged and configured to be coupled to a fluid source;
- a fluid output port arranged and configured to deliver fluid proximate the curvilinear cutting tip; and
- a fluid channel fluidly coupling the fluid input port to the fluid output port for supplying fluid from the fluid source through the fluid input port to the fluid output port.

24. A method, comprising:
- operating, via a user interface, an actuation mechanism with a piezoelectric element comprised in a body to cause motion in a cutting tip; and
- extending the cutting tip, wherein the cutting tip is configured to match a curvature of an acetabular cup.

25. The method of claim 24, further comprising causing fluid to exit a fluid output port proximate the cutting tip based on operation of the user interface.

26. The method of claim 24, further comprising operating the user interface to extend the cutting tip.

27. The method of claim 24, wherein extension of the cutting tip is configured to follow the curvature of the acetabular cup.

28. The method of claim 24, further comprising controlling one or more of amplitude and frequency of motion in the cutting tip based on operation of the user interface.

* * * * *